United States Patent [19]

Saint-Ruf et al.

[11] 3,940,387

[45] Feb. 24, 1976

[54] YOHIMBINE DERIVATIVES, PROCESS FOR THEIR PREPARATION AND THEIR APPLICATIONS

[76] Inventors: Germain Saint-Ruf, 83 Rue de l'Egalite, 45 Olivet; Pham Huu Chanh, 84, Rue du Muret, 31 Toulouse, both of France; Buu Hoi, late of Paris, France

[22] Filed: May 5, 1972

[21] Appl. No.: 250,807

[30] Foreign Application Priority Data

May 6, 1971 France.............................. 71.16350

[52] U.S. Cl. ... 260/240 AL; 260/286 R; 260/287 A; 424/258
[51] Int. Cl.............................................. C07d 33/56
[58] Field of Search .................. 260/287 A, 140 AL

[56] References Cited
UNITED STATES PATENTS

| | | | |
|---|---|---|---|
| 2,702,325 | 11/1972 | Fellian | 260/287 A |
| 2,726,243 | 1/1955 | Huebner | 260/287 A |
| 2,933,500 | 4/1960 | Rudner | 260/288 R |

*Primary Examiner*—Donald G. Daus
*Assistant Examiner*—David E. Wheeler
*Attorney, Agent, or Firm*—Young & Thompson

[57] ABSTRACT

The present invention relates to yohimbine derivatives. Said derivatives have the general formula

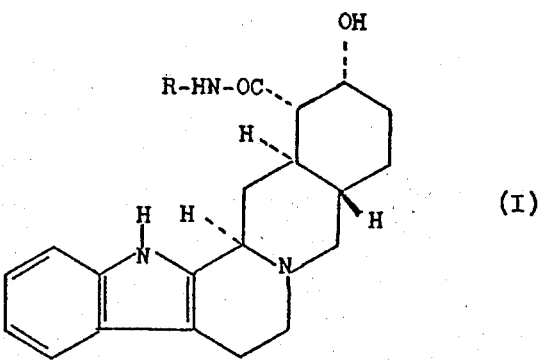

(I)

in which R is a radical

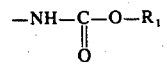

or

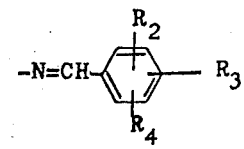

$R_1$ being an alkyl, aralkyl, alkylaryl, aryl group optionally carrying a nitro group, $R_2$, $R_3$ and $R_4$ being hydrogen, a hydroxy, alkoxy or mono- or dialkylamino group.

They possess hypotensive and cardio-stimulant properties.

3 Claims, No Drawings

YOHIMBINE DERIVATIVES, PROCESS FOR THEIR PREPARATION AND THEIR APPLICATIONS

This invention relates to yohimbine derivatives, to a process for their preparation and to the applications thereof, particularly their therapeutic applications.

Thus, the invention relates to yohimbine derivatives having the formula:

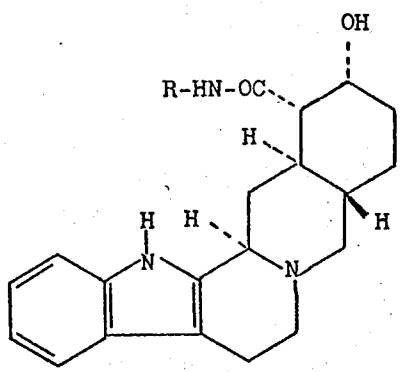

in which R is a radical

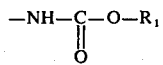

or

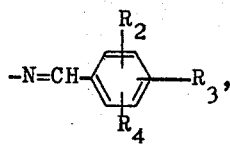

$R_1$ being an alkyl, aralkyl, alkylaryl radical or an aryl radical optionally carrying a nitro group, $R_2$, $R_3$ and $R_4$ being independently from each other hydrogen, a hydroxy, alkoxy or mono- or dialkyl-amino group.

The alkyl radicals and the alkyl moieties of the alkoxy radicals within the above definition are preferably lower radicals having 1–12 carbon atoms and preferably 1–6 carbon atoms.

The aryl radicals are typically phenyl radicals.

The invention includes also within its scope the acid addition salts of derivatives (I), for example those obtained by dissolving derivatives (I) in free base form in a stoichiometrically equivalent amount of hydrochloric, hydrobromic, sulfuric, phosphoric, methanesulfonic, maleic, succinic, acetic, oxalic, lactic, tartaric acid, and the like.

Derivatives (I) possess hypotensive and cardiostimulant properties. The invention contemplates also the therapeutic use of derivatives (I).

The derivatives of the formula (I) may be prepared by reaction of yohimbic acid hydrazide either with an alkyl, alkylaryl, arylalkyl or aryl haloformate of the formula

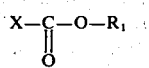

in which $R_1$ has the aforesaid meaning and X is halogen, to give derivatives of the formula (I) in which R is a radical

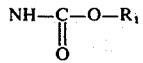

or with an aldehyde having the formula

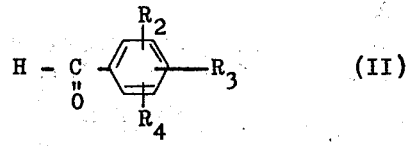

in which $R_2$, $R_3$ and $R_4$ have the aforesaid meaning, to give derivatives of the formula (I) in which R is a radical

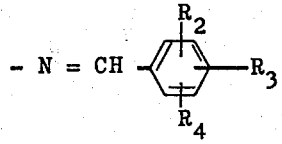

The yohimbic acid hydrazide used as starting material may be obtained by the action of hydrazine hydrate on yohimbine or one of its acid addition salts.

Yohimbine is a known material which was extracted from certain plants such as Corynanthe Johimbe, Rubiaceae and Apocynaeae (cf. J. Pharm. Chim. 19. 209, 1934; Helv. Chim. Acta 37, 849, 1954; J. Am. Chem. Soc. 76, 1695, 1954) and the synthesis of which is described by Van Tamelen et al in J. Am. Chem.Soc., 80, 5006, 1958 or by Izantay et al, Tetrahedron Letters, 1665, 1965.

A chloroformate is preferably used for the reaction of yohimbic acid with a haloformate of the formula

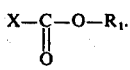

The reaction may be carried out in refluxing alcohol solution, during 5–60 minutes.

The reaction of yohimbic acid hydrazide with the aldehyde having the formula (II) may be carried out by refluxing the reagents dissolved in an alcohol, advantageously in the presence of traces of an acid.

The following examples illustrate the invention:

EXAMPLE 1 a. Preparation of yohimbic acid hydrazide or yohimbohydrazide

A solution of yohimbine hydrochloride (4 g) and excess (about 5 to about 10 ml) 98% hydrazine hydrate in absolute ethanol (75 ml) is refluxed during 24 hours. The resulting hydrazide solution is then concentrated, diluted with water and the resulting precipitate is then suction filtered, to give, after recrystallization from aqueous ethanol, colorless prismatic needles of yohimbohydrazide hydrate, melting at 170°–172°C with loss of crystallization water and with resolidification, with a second melting at 292°C.

Analysis for $C_{20}H_{26}N_4O_2$, $H_2O$: Calculated: C 64.5; H 7.6; N 15.0; Found: C 64.6; H 7.3; N 14.8.

b. Preparation of the derivative in which $R_2$ = methoxy at meta-position, $R_3$ = hydroxy at para position, $R_4$ = H A solution of yohimbohydrazide hydrate (37.2 g) and vanillin (15.2 g) in absolute ethanol (750 ml) is refluxed during 12 hours. After evaporating off the solvent, the solid residue is taken up into benzene to give, with a yield of about 90%, colorless prisms of hydrazone I melting at 210°C. $[\alpha]_D^{20} = +88°$ (c = 1, in ethanol).

Analysis for $C_{28}H_{32}N_4O_4$: Calculated: C 68.8; H 6.6; N 11.5; Found: C 68.7; H 6.5; N 11.3.

EXAMPLE 2

($R_2$ = methoxy at para-position, $R_3 = R_4 = H$)

a. A solution of yohimbohydrazide (3.72 g) and anisaldehyde (1.36 g) in absolute ethanol (75 ml) is refluxed during 3 hours in the presence of one drop of acetic acid. After evaporating off the solvent in vacuo, the resulting solid residue is recrystallized from benzene to give, with a yield of 70–80%, fine needles of hydrazone I melting at 198°C, $[\alpha]_D^{20} = +81.5°$ (c 1, ethanol)

Analysis for $C_{28}H_{32}N_4O_3$: Calculated: C 71.2; H 6.8; Found: C 70.9; H 6.8.

b. Resulting hydrazone I is dissolved in ethanol and a stoichiometrically equivalent amount of hydrochloric acid is added thereto, to give the hydrochloride which melts at 255°C.

c. Operating as described under (b) and substituting acetic acid for hydrochloric acid gives the acetate which melts at 242°C.

EXAMPLE 3

($R_2 = R_3$ = methoxy at 2- and 5-positions, $R_4 = H$)

A solution of yohimbic acid hydrazide (6 g) and 2,5-dimethoxybenzaldehyde (2.82 g) in absolute ethanol (75 ml) is refluxed during 3 hours in the presence of a drop of acetic acid; after evaporating off the solvent in vacuo, the residue is recrystallized from benzene, to give fine cream-colored needles which melt at 191°C, $[\alpha]_D^{20} = +33.4°$ (c 1, ethanol).

Analysis for $C_{29}H_{34}N_4O_4$: Calculated: C 69.3; H 6.8; Found: C 69.3; H 6.9.

EXAMPLE 4

($R_2 = R_3 = R_4$ = methoxy at 3-, 4- and 5-positions)

This hydrazone is obtained under the same conditions as the preceding compound, from 3,4,5-trimethoxy-benzaldehyde. After recrystallization from benzene, it is obtained in the form of cream-colored microcrystals which melt at 240°C, $[\alpha]_D^{20} = +57.4°$ c 1, ethanol)

EXAMPLE 5

($R_2$ = methoxy at meta-position, $R_3 = R_4 = H$)

Operating as described in Example 3 and using 3-methoxybenzaldehyde as aldehyde, there is obtained the corresponding hydrazone whose crystals, after recrystallization from benzene, melt at 189°C, $[\alpha]_D^{20} = +52.8°$ (c 1, ethanol)

EXAMPLE 6

($R_2 = R_3$ = methoxy at 2- and 3-positions, $R_4 = H$)

Operating as in Example 3 and using an aldehyde 2,3-dimethoxy-benzaldehyde, there is obtained the corresponding hydrazone whose crystals, after recrystallization from benzene, melt at 201°C. $[\alpha]_{589m\mu}^{20} = +15.5°$ (c 1, ethanol).

EXAMPLE 7

($R_2$ = dimethylamino at para-position, $R_3 = R_4 = H$)

The procedure of Example 2 is used, with yohimbohydrazide (3.54 g) and p-dimethylaminobenzaldehyde (1.49 g); the hydrazone crystallizes from ethyl acetate to give fine cream-colored needles which melt at 225°C.

EXAMPLE 8

($R_1$ = ethyl)

A solution of yohimbohydrazide hydrate (37.2 g) and ethyl chloroformate (13 g) in absolute ethanol (750 ml) is stirred during a period of time of about one to about two hours, and is then refluxed over a water-bath during 10–20 minutes. After cooling, the reaction mixture is poured into a 5% aqueous caustic soda solution, the resulting precipitate is suction filtered, washed with water and recrystallized from a mixture of benzene and ethanol, to give the desired compound, in a yield of 90%, in the form of colorless prisms melting at 185°C. $[\alpha]_D^{25} = +43.7°$ (c 1, ethanol).

Analysis for $C_{23}H_{30}N_4O_4$: Calculated: C 64.6; H 7.1; N 13.1; Found: C 64.4; H 7.1; N 12.8.

EXAMPLE 9

The procedure of Example 8, carried out with isopropyl chloroformate, gives compound (I) in which $R_1 = -CH(CH_3)_2$ which is recrystallized from a mixture of benzene and ethanol, to give substantially colorless fine needles, M.p. = 210°C. $[\alpha]_D^{25} = +44.6°$ (c 1, ethanol).

EXAMPLE 10

Compound (I) in which $R_1$ is $-C_6H_5$, obtained from phenyl chloroformate under experimental conditions analogous to those of Example 8, gives cream-colored needles on crystallization from ethanol containing added ligroin, which needles melt at 218°C and then re-solidify to melt again at 280°C. $[\alpha]_{589m\mu}^{25} = 35.4°$ (c 1, ethanol).

EXAMPLE 11

The compound obtained from benzyl chloroformate crystallizes from ethanol with added petroleum ether, to give cream-colored needles, m.p. = 227°C. $[\alpha]_{546m\mu}^{25} = +40.1°$ (c, 1, ethanol).

EXAMPLE 12

Compound (I) in which $R_1$ is $-CH_2-C_6H_4NO_2$ (p) is prepared from p-nitrobenzyl chloroformate and crystallizes from ethanol + petroleum ether to give fine cream-colored needles, m.p. = 196°–197°C. $[\alpha]_{589\,m\mu}^{25} = +100.8°$ (c 1, ethanol)

The results of pharmacological and toxicological tests demonstrate the highly interesting properties of the derivatives of this invention.

I — PHARMACOLOGICAL PROPERTIES

The experimentation was carried out with chloralose-anesthetized dogs (100 mg/kg by the intravenous route).

The systemic blood pressure was recorded at the level of the right *a. femoralis* by means of a Statham P23AA electromanometer. The rate of flow and the rhythm of ventilation are measured with a Dräger recording volumeter. Oxygen pressure $pO_2$ is measured polarographically; are also measured: the carbon dioxide pressure $pCO_2$ and the pH of the blood (both arterial and venous), together with the oxygen and carbon dioxide pressures of the gas breathed out.

The cardiac rate of flow was recorded using the method according to FICK.

The contractile strength of the heart was recorded by means of a strain gage attached to the wall of the right ventricle. The rate of increase of the isometric tension of the myocardium was evaluated by differentiation of the contractile strength of the heart; the cardiac rhythm was recorded by means of a cardiotachometer and the electrocardiogram was recorded by means of a Cardioline electrocardiograph.

The derivatives according to the present invention were administered either as a solution in normal saline solution through the saphenous vein or suspended in gummy julep, by the intraduodenal route, via a retaining catheter.

The variations of the various parameters after a single administration were investigated as a function of time.

a. Systemic hemodynamics

Both on intravenous (1 mg/kg I.V.) and on intraduodenal (5 mg/kg, I.D.) administration, the derivatives according to the invention exhibited no significant hypotensive effect; however they produce a substantial reduction of peripheral strength and of elastic strength of the arteries.

The derivatives according to the invention increase substantially the cardiac rate of flow, the systolic rate of ejection, the cardiac and systolic indices, the work of the left ventricle and the systolic ejection work. Said enhanced performances of the heart are considerable when the compounds are administered intravenously (1 mg/kg, I.V.) and still quite substantial on intraduodenal (5 mg/kg, I.D.) administration. Finally, the compounds do not increase noticeably the oxygen requirements of the myocardium.

b. Contractile strength of the heart

The derivatives according to the invention stimulate strongly the contractile strength of the heart of dogs under chloralose-induced anesthesia. With a single 1 mg/kg dose administered intravenously, the increase of the contractile strength of the heart may attain and even exceed 100% and lasts more than one hour; on intraduodenal administration (5 mg/kg, I.D.) it is of the order of 30% and lasts more than 2 hours. The rate of increase of the isometric tension of the myocardium is considerably stimulated by the action of the compounds investigated; it exceeds 140% on intraduodenal administration of 5 mg/kg of the test compounds.

II — TOXICITY a. Immediate and delayed toxicity on administration of a single dose The tests were carried out with white male rats weighing 115 ± 10 g and with white male mice weighing 21 ± 1 g. After a fasting period of 18 hours, the animals were separated into homogeneous lots of 10 animals.

The derivatives according to the present invention, suspended in gummy julep (gum arabic 3 g/100 ml), at concentrations of 25 and 50 g/100 ml, were administered orally (through a gastric catheter) at a uniform volume of 1 ml/100 g of rat and of 0.2 ml/20 g of mouse. Two dosages were tested: 2.5 and 5 g/kg (10 animals per dosage).

The treated animals were kept under observation during 14 days.

At doses of 2.5 and 5 g/kg by the oral route, the death rate due to the test compounds was nil, both immediately after administration and after a period of observation of 14 days. Also, the treated animals exhibited no apparent variation in their behavior.

b. Medium term delayed toxicity on administration of repeated daily doses

The test involved white male rats weighing from 130 to 140 g at the beginning of the experiment.

The animals were separated into two homogeneous lots:

Lot I: reference animals given only solvent, viz.: gummy julep.

Lot II: animals given the test compounds, at a dosage of 100 mg/kg/day.

The derivatives according to the invention, suspended in gummy julep (gum arabic, 3 g/100 ml) at a concentration of 1 g/100 ml), were administered orally through a gastric catheter at a rate of 1 ml/100 g of body weight. The administration was repeated daily, 6 times a week, during a period of time of 45 days.

The animals thus treated were kept under observation in a room maintained thermostatically at a temperature of 24±1°C. The behavior of the animals was noted daily, and the animals were weighed twice a week.

At the end of the experiment, the following tests were carried out on each animal:

hematologic tests biochemical blood tests (glucose, urea, cholesterol, SGOT and SGPT transaminases, alkaline phosphatases), pathological examinations.

On repeated daily administration at a dosage of 100 mg/kg/day, the derivatives according to the invention produce neither fatal issues nor any significant modification of behavior, weight increase, erythrocyte and leukocyte count, leycocytic picture, glycemia, uremia, cholesterolemia, alkaline phosphatasemia and SGOT and SGPT transaminasemia.

On the other hand, they cause no microscopically detectable cell deterioration.

It is apparent from such tests that the derivatives according to the invention may be profitably used as active ingredient in drugs having an action on the cardiovascular system.

Said derivatives may be administered systemically, orally or parenterally. The daily dosage regimen is from 10 mg to 100 mg of active ingredient per 24 hours. Examples of suitable formulations are given below:

| Tablets | weak dose | strong dose |
|---|---|---|
| Active ingredient | 5 mg | 25 mg |
| Excipient Talc | | |
| Lactose | q.s. for one tablet | |
| Magnesium stearate | | |

Injectable ampoules

Active ingredient (hydrochloride) . . . 25 mg
Normal saline solution . . . q.s. for one ampoule

Having now described our invention what we claim as new and desire to secure by Letters Patent is:

1. The compound of formula

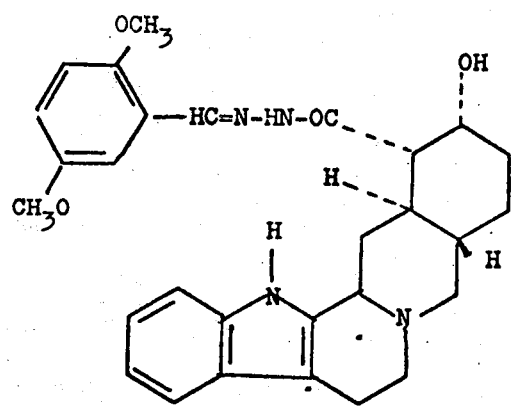

and its pharmaceutically acceptable acid addition salts.

2. The compound of formula

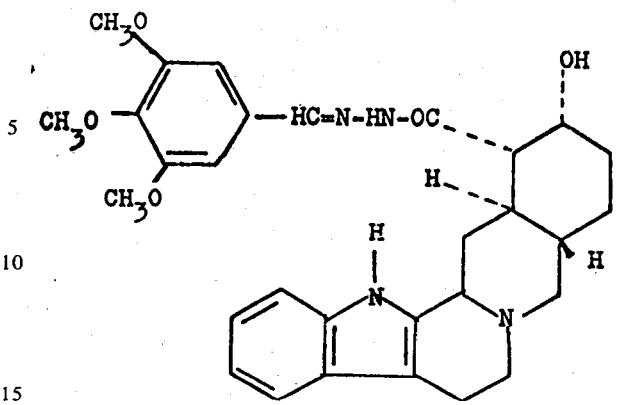

and its pharmaceutically acceptable acid addition salts.

3. The compound of formula and its pharmaceutically acceptable acid addition salts.

* * * * *